United States Patent [19]

Flint et al.

[11] 4,407,671

[45] Oct. 4, 1983

[54] USE OF 3-AMINOCYCLOHEXADIENECARBOXYLIC ACIDS FOR CONTROLLING THE GROWTH OF UNWANTED PLANTS

[75] Inventors: Dennis H. Flint; Herbert Estreicher, both of Modesto, Calif.

[73] Assignee: Shell Oil Company, Houston, Tex.

[21] Appl. No.: 447,379

[22] Filed: Dec. 6, 1982

[51] Int. Cl.$^3$ ............................................. A01N 37/08
[52] U.S. Cl. ......................................... 71/113; 71/108
[58] Field of Search .......................... 71/113, 107, 118

[56] References Cited

U.S. PATENT DOCUMENTS 4,187,316  2/1980  Metcalf et al. ...................... 424/305

FOREIGN PATENT DOCUMENTS 2012268  7/1979  United Kingdom .

Primary Examiner—Catherine L. Milis

[57] ABSTRACT

Growth of unwanted plants is controlled by certain 3-aminocyclohexadienecarboxylic acids.

1 Claim, No Drawings

USE OF 3-AMINOCYCLOHEXADIENECARBOXYLIC ACIDS FOR CONTROLLING THE GROWTH OF UNWANTED PLANTS

DESCRIPTION OF THE INVENTION

It has been found that certain 3-aminocyclohexadienecarboxylic acids, their salts and lower alkyl esters adversely affect the growth of plants to which they have been applied, and thus are useful for controlling the growth of unwanted plants. These acids are described generally as 3-aminocyclohexadienylcarboxylic acids in which the carbon atom of the ring to which the carboxyl moiety is bonded is olefinically unsaturated, and the carbon atom of the ring to which the amino moiety is bonded is saturated, their salts and lower alkyl esters.

This generic description defines three isomeric acids:

(I) 3-amino-4,6-cyclohexadienecarboxylic acid, of the formula

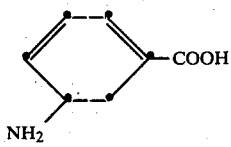

(II) 3-amino-1,5-cyclohexadienecarboxylic acid, of the formula

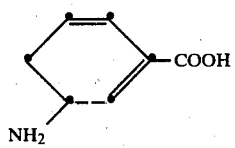

(III) 3-amino-1,4-cyclohexadienecarboxylic acid, of the formula

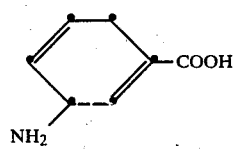

All three are known compounds. Isomer I is a natural product known as gabaculine. References to it in the art are summarized in U.S. Pat. No. 4,187,316. That patent also discloses Isomer II, and a method for its preparation (Example 3 of the patent). Isomer III, and a method for its preparation are shown in British Pat. No. 2,012,268 (in Example 4 thereof). Since the carbon atom at the 3-position of the ring is an asymmetric center, the compounds are chiral and exist in the form of optical isomers. The individual isomers, which may have different activity with respect to plants, have not been isolated and tested. The invention includes all of the active isomers and mixtures thereof—both those arising from the methods of preparation used, and those that are deliberately created.

The contemplated esters are those of lower straight-chain and branched-chain alkanols—i.e., those containing from one to six carbon atoms.

The contemplated salts are those of alkali metals, alkaline earth metals, and amines, and ammonium salts. Suitable amine salts include those of alkyl- and alkanolamines, including mono-, di- and tri-alkyl and alkanol amines wherein each alkyl moiety contains from one to twenty carbon atoms.

Compounds of this class have been found to adversely affect the growth of plants, and therefore to be useful for controlling the growth of unwanted plants. They appear to be equally toxic to both broad-leaved plants and grasses.

Accordingly, the invention includes a method of combating unwanted plants at a locus which comprises applying to the locus an effective amount of a 3-aminocyclohexadienylcarboxylic acid or salt or ester thereof as described above. For application, the compound generally is applied most effectively by formulating it with a suitable inert carrier or surface-active agent, or both.

The term "carrier" as used herein means an inert solid or fluid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, koalinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; bitumen; waxes such as, for example, beeswax, paraffin wax, and chlorinated mineral waxes; solid fertilizers, for example, supherphosphates; and ground, naturally-occurring, fibrous materials, such as ground corncobs.

Examples of suitable fluid carriers are water, alcohols such as, for example, isopropyl alcohol, glycols; ketones such as, for example, acetone, methyl ethyl ketone, methyl isobutyl ketone, isophorone and cyclohexanone; ethers such as, for example, cellosolves; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied, normally vaporous, gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 9 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25, 50 or 75% by weight of the active compound and usually contain, in addition to the solid carrier, 3–10% by weight of a dispersing agent, 15% of a surface-active agent and, where necessary, 0–10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5–10% by weight of the active compound. Granules are usually prepared to have a size between 10 and 100 BS mesh (1.676–0.52) mm), and may be manufactured by agglomeration or impregnation techniques. Generally, granules will contain 0.5–25% by weight of the active compound, 0–1% by weight of additives such as stabilizers, slow release modifiers and binding agents. Emulsifiable concentrates usually contain, in addition to the solvent and, when necessary, cosolvent, 10–50% weight per volume of the active compound, 2–20% weight per volume emulsifiers and 0–20% weight per volume of appropriate additive such as stabilizers, penetrants and corrosion inhibitors. Suspension concentrates are compounded so as to obtain a stable, non-sedimenting, flowable product and usually contain 10–75% weight of the active compound, 0.5–5% weight of dispersing agents, 1–5% of surface-active agent, 0.1–10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have a thick, mayonnaise-like consistency.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying the active compound, ordinarily in a composition of one of the aforementioned types, to soil in which the seeds of the unwanted plants are present, or to the foliage of the unwanted plants. The active compound, of course, is applied in an amount sufficient to exert the desired action.

The amount of the active compound to be used in combating undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound will be satisfactory.

EXAMPLES OF ACTIVITY WITH RESPECT TO PLANTS

In the following examples, the species of plants that were tested were:
Barnyardgrass (watergrass)—*Echinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

TEST PROCEDURES

The preemergence (soil) herbicidal activity of the compounds was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions and temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of compounds of the invention was evaluated by spraying 10-day-old large downy brome plants in some cases, 6-day-old Johnsongrass plants in other cases, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The spray plants were held under controlled conditions of temperature, moisture and light for 7 to 8 days and the effect of the test compound was then evaluated visually, the results being rated on the 0 to 9 scale described above.

The compounds that were tested were Isomers I and III.

Results of the preemergence and postemergence herbicidal activity tests are set forth in Table I.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Compound | Barnyard-grass | Garden cress | Downy brome | Velvet-leaf | Yellow foxtail | Sickle-pod | Crab-grass | Pig-weed | Johnson-grass | Velvet-leaf | Yellow foxtail | Sickle-pod |
| I | 9 | 7 | 9 | 9 | 8 | 9 | 8 | 8 | 7 | 7 | 7 | 8 |
| III | 8 | 8 | 6 | 7 | 6 | 2 | 8 | 7 | 4 | 3 | 4 | 3 |

We claim:

1. A method for controlling growth of unwanted plants at a locus which comprises applying to that locus an effective amount of a 3-aminocyclohexadienecarboxylic acid in which the carbon atom of the ring to which the carboxyl moiety is bonded is olefinically unsaturated, and the carbon atom of the ring to which the amino moiety is bonded is saturated, an alkali metal, alkaline earth metal, ammonium or amine salt, or a $C_1$–$C_6$ alkyl ester, of such an acid.

* * * * *